(12) United States Patent
Masumoto

(10) Patent No.: US 10,085,672 B2
(45) Date of Patent: Oct. 2, 2018

(54) DIAGNOSTIC ENDOSCOPIC IMAGING SUPPORT APPARATUS AND METHOD, AND NON-TRANSITORY COMPUTER READABLE MEDIUM ON WHICH IS RECORDED DIAGNOSTIC ENDOSCOPIC IMAGING SUPPORT PROGRAM

(71) Applicant: FUJIFILM Corporation, Tokyo (JP)

(72) Inventor: Jun Masumoto, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 741 days.

(21) Appl. No.: 14/337,867

(22) Filed: Jul. 22, 2014

(65) Prior Publication Data

US 2014/0336501 A1 Nov. 13, 2014

Related U.S. Application Data

(63) Continuation of application No. PCT/JP2013/000184, filed on Jan. 17, 2013.

(30) Foreign Application Priority Data

Jan. 24, 2012 (JP) ................................ 2012-011865

(51) Int. Cl.
*A61B 5/06* (2006.01)
*A61B 6/12* (2006.01)
(Continued)

(52) U.S. Cl.
CPC ............ *A61B 5/066* (2013.01); *A61B 1/0005* (2013.01); *A61B 1/00006* (2013.01);
(Continued)

(58) Field of Classification Search
CPC .................................................... A61B 5/066
See application file for complete search history.

(56) References Cited

U.S. PATENT DOCUMENTS 7,224,827 B2 * 5/2007 Acar ......................... G06T 3/40
378/21
8,672,836 B2 * 3/2014 Higgins ............. A61B 1/00009
345/427
(Continued)

FOREIGN PATENT DOCUMENTS

JP 2000-135215 A 5/2000
JP 2002-369790 A 12/2002
(Continued)

OTHER PUBLICATIONS

Byun et al., Pattern Recognition, vol. 29, No., pp. 1297-1307, 1996.*
(Continued)

*Primary Examiner* — Katherine Fernandez
*Assistant Examiner* — Yi-Shan Yang
(74) *Attorney, Agent, or Firm* — McGinn I.P Law Group, PLLC.

(57) ABSTRACT

A diagnostic endoscopic imaging support apparatus includes a three-dimensional image data obtaining section that obtains three-dimensional image data of a subject, a tubular tissue shape data obtaining section that extracts and obtains tubular tissue shape data representing a shape of a tubular tissue in the subject from the three-dimensional image data obtained by the three-dimensional image data obtaining section, an endoscope route data obtaining section that obtains endoscope route data representing a route of an endoscope inserted into the subject, and a matching section that performs matching between the tubular tissue shape data and the endoscope route data.

19 Claims, 8 Drawing Sheets

(51) Int. Cl.
*A61B 1/00* (2006.01)
*A61B 1/04* (2006.01)
*A61B 1/267* (2006.01)
*A61B 1/31* (2006.01)
*A61B 6/03* (2006.01)
*A61B 5/055* (2006.01)
*G01R 33/28* (2006.01)

(52) U.S. Cl.
CPC ........ *A61B 1/00055* (2013.01); *A61B 1/041* (2013.01); *A61B 1/2676* (2013.01); *A61B 1/31* (2013.01); *A61B 6/032* (2013.01); *A61B 6/12* (2013.01); *A61B 5/055* (2013.01); *G01R 33/285* (2013.01)

(56) References Cited

U.S. PATENT DOCUMENTS

| | | | |
|---|---|---|---|
| 2002/0022765 A1 | 2/2002 | Belson | |
| 2002/0062062 A1 | 5/2002 | Belson et al. | |
| 2006/0152516 A1* | 7/2006 | Plummer | G06F 19/321 345/538 |
| 2006/0195033 A1 | 8/2006 | Akimoto et al. | |
| 2007/0286493 A1* | 12/2007 | Liu | G06K 9/481 382/203 |
| 2008/0207997 A1* | 8/2008 | Higgins | A61B 1/00009 600/114 |
| 2009/0227861 A1* | 9/2009 | Ganatra | A61B 34/20 600/424 |
| 2011/0245660 A1* | 10/2011 | Miyamoto | A61B 6/032 600/424 |
| 2012/0046521 A1* | 2/2012 | Hunter | A61B 1/2676 600/104 |
| 2013/0046137 A1* | 2/2013 | Zhao | A61B 1/00181 600/102 |

FOREIGN PATENT DOCUMENTS

| | | |
|---|---|---|
| JP | 2003-245242 A | 9/2003 |
| JP | 2004-551 A | 1/2004 |
| JP | 2005-503882 A | 2/2005 |
| JP | 2005-304937 A | 11/2005 |
| JP | 2006-149972 A | 6/2006 |
| JP | 2006-198031 A | 8/2006 |
| JP | 2007-7180 A | 1/2007 |
| JP | 2010-517632 A | 5/2010 |
| JP | 2010-172350 A | 8/2010 |
| WO | WO 2008/095068 A1 | 8/2008 |
| WO | WO 2010113097 A1 * | 10/2010 ........... A61B 1/0005 |

OTHER PUBLICATIONS

Mokhtarian et al., 1986, IEEE Trans PAMI vol. 8, No. 1, pp. 34-43.*
Nagura et al., "Partial Contour Processing Using Curvature Function-Assembly of Jigsaw Puzzle and Recognition of Moving Figures". Systems and Computers in Japan. 1986, vol. 17, No. 2, pp. 30-39.*
International Search Report (ISR) (PCT Form PCT/ISA/210), in PCT/JP2013/000184, dated Apr. 2, 2013.
T. Yamaguchi et al., "Oblique-viewing Endoscopic Navigation System with Simultaneous Display of Virtual and Real Endoscopic Images", Technical Report of IEICE, MI, Medical Image, vol. 103, Issue 213, pp. 43-46, 2003 and a partial English translation thereof.
Japanese Office Action dated Feb. 17, 2015 with a partial English translation thereof.

* cited by examiner

DIAGNOSTIC ENDOSCOPIC IMAGING SUPPORT APPARATUS AND METHOD, AND NON-TRANSITORY COMPUTER READABLE MEDIUM ON WHICH IS RECORDED DIAGNOSTIC ENDOSCOPIC IMAGING SUPPORT PROGRAM

CROSS-REFERENCE TO RELATED APPLICATIONS

This application is a Continuation of PCT International Application No. PCT/JP2013/000184 filed on Jan. 17, 2013, which claims priority under 35 U.S.C. § 119 (a) to Japanese Patent Application No. 2012-011865 filed on Jan. 24, 2012. Each of the above application(s) is hereby expressly incorporated by reference, in its entirety, into the present application.

BACKGROUND OF THE INVENTION

Technical Field

The present invention relates to a diagnostic endoscopic imaging support apparatus and method, and a non-transitory computer readable medium on which is recorded a diagnostic endoscopic imaging support program, capable of identifying an actual tip position of an endoscope in a three-dimensional image of a subject obtained in advance.

Background Art

Recently, the technology of observing and treating tubular tissues of patients, such as large intestines, small intestines, bronchi, and the like, has been drawing attention.

While endoscopic imaging may provide vivid images of the colors and textures in the tubular tissues represented by image sensors, such as a CCD (Charge Coupled Device) and the like, it represents interiors of the tubular tissues as a two-dimensional image, so that it is difficult to understand which position of the tubular tissue the image indicates.

Consequently, technology in which a route to a target point within a tubular tissue is obtained in advance using three-dimensional image data obtained in advance through tomographic imaging by a modality, such as CT (Computed Tomography) or the like, then a virtual endoscopic image which is similar to an endoscopic image actually obtained by an endoscope is generated using the aforementioned three-dimensional image data, and the route to the target point is navigated using the virtual endoscopic image is proposed (refer to Japanese Unexamined Patent Publication No. 2006-198031 and Japanese Unexamined Patent Publication No. 2000-135215).

When displaying a virtual endoscopic image like that described above, it is necessary to identify the position in the three-dimensional image data corresponding to the tip position of the endoscope actually inserted into the tubular tissue. Consequently, for example, T. Yamaguchi et al., "Oblique-viewing Endoscopic Navigation System with Simultaneous Display of Virtual and Real Endoscopic Images", Technical Report of IEICE, MI, Medical Image, Vol. 103, Issue 213, pp. 43-46, 2003 proposes the use of an optical sensor or a magnetic sensor in order to identify the actual tip position of the endoscope in a tubular tissue.

Further, in order to identify the position of an endoscope as in T. Yamaguchi et al., "Oblique-viewing Endoscopic Navigation System with Simultaneous Display of Virtual and Real Endoscopic Images", Technical Report of IEICE, MI, Medical Image, Vol. 103, Issue 213, pp. 43-46, 2003, many methods are proposed in which the endoscope is provided with a marker which can be detected by a sensor and the camera position is identified by detecting the marker.

Further, Japanese Unexamined Patent Publication No. 2006-149972, Japanese Unexamined Patent Publication No. 2007-007180, and Japanese Unexamined Patent Publication No. 2003-245242, Japanese Unexamined Patent Publication No. 2004-000551, and Japanese Unexamined Patent Publication No. 2002-369790 propose methods for sensing what shapes the flexible endoscopes inserted into the bodies have.

Conventionally, the tip position of an endoscope is tracked, for example, by a magnetic sensor and, by considering the relative position between the pre-operation image and in-operation image, the position in the pre-operation image which is deemed to be the same as the tip position of the endoscope during operation is identified, and the virtual endoscopic image of the identified position is displayed.

DISCLOSURE OF THE INVENTION

If it is assumed that tubular tissues, such as large intestines are stationary before and during operations, the methods described above may display virtual endoscopic images corresponding to actual tip positions of endoscopes, but soft tissues such as large intestines accompany deformations, thereby often causing problems that positions of virtual endoscopic images deviate from actual tip positions of endoscopes.

Further, a tubular tissue, such as a large intestine, has a complexly curved shape in a front-back direction and a right-left direction of the subject, and a two- or three-folded shape in a front-back direction of the subject. Therefore, it has been very difficult to accurately identify the actual tip positions of endoscopes at the folded portions in pre-operation images, since the use of the sensing technology described above can identify only tip positions of endoscopes.

In view of the circumstances described above, it is an object of the present invention to provide a diagnostic endoscopic imaging support apparatus and method, and a non-transitory computer readable medium on which is recorded a diagnostic endoscopic imaging support program capable of accurately identifying a tip position of an endoscope in a three-dimensional image of a subject obtained in advance.

A diagnostic endoscopic imaging support apparatus of the present invention includes a three-dimensional image data obtaining section that obtains three-dimensional image data of a subject, a tubular tissue shape data obtaining section that extracts and obtains tubular tissue shape data representing a shape of a tubular tissue in the subject from the three-dimensional image data obtained by the three-dimensional image data obtaining section, an endoscope route data obtaining section that obtains endoscope route data representing a route of an endoscope inserted into the subject, and a matching section that performs matching between the tubular tissue shape data and the endoscope route data.

The diagnostic endoscopic imaging support apparatus described above may include a display control section that displays the route of the endoscope in the subject within a three-dimensional stereoscopic image of the tubular tissue based on the three-dimensional image data, the endoscope route data, and a result of the matching in the matching section.

Further, the diagnostic endoscopic imaging support apparatus described above may include a display control section that displays the route of the endoscope in the subject within a cross-sectional image of the tubular tissue based on the three-dimensional image data, the endoscope route data, and a result of the matching in the matching section.

Still further, the matching section may perform the matching in real time when the route of the endoscope in the subject is changed.

Further, when the route of the endoscope in the subject is changed, the matching section may obtain a variation in the shape and perform the matching using the variation.

Still further, the tubular tissue shape data obtaining section may obtain tree structure data as the tubular tissue shape data, and the matching section may perform matching using the tree structure data.

Further, the endoscope route data obtaining section may obtain line segment structure data as the endoscope route data, and the matching section may perform matching of local maximum points of curvature between the line segment structure data and the tree structure data.

Still further, the matching section may obtain information of distance from the insertion opening of the endoscope to the tip of the endoscope inserted into the subject and perform the matching using the information of distance.

Further, the display control section may display the tubular tissue as a surface model.

Still further, the display control section may display the tubular tissue as a voxel model.

Further, the diagnostic endoscopic imaging support apparatus described above may include a tip position information obtaining section that obtains tip position information of the endoscope in a coordinate of the three-dimensional image data based on a result of the matching in the matching section, a virtual endoscopic image data obtaining section that obtains virtual endoscopic image data virtually generated on the assumption that imaging is performed at the tip position of the endoscope based on the tip position information obtained by the tip position information obtaining section and the three-dimensional image data, and a display control section that displays a virtual endoscopic image based on the virtual endoscopic image data and a real endoscopic image actually captured by the endoscope.

Still further, the display control section may display the virtual endoscopic image and the real endoscopic image side-by-side.

Further, the display control section may display the virtual endoscopic image within the display screen of the real endoscopic image.

Still further, the display control section may perform a blending display of the real endoscopic image and the virtual endoscopic image.

Further, a bronchoscope, a large intestine endoscope, a small intestine endoscope, or a capsule endoscope may be used as the endoscope.

Still further, the tubular tissue may be a bronchus, a large intestine, or a small intestine.

Further, CT image data may be used as the three-dimensional image data.

Still further, MR image data may be used as the three-dimensional image data.

A diagnostic endoscopic imaging support method of the present invention includes the steps of obtaining three-dimensional image data of a subject, extracting and obtaining tubular tissue shape data representing a shape of a tubular tissue in the subject from the three-dimensional image data, obtaining endoscope route data representing a route of an endoscope inserted into the subject, and performing matching between the tubular tissue shape data and the endoscope route data.

A non-transitory computer readable medium on which is recorded a diagnostic endoscopic imaging support program of the present invention is a non-transitory computer readable medium on which is recorded a diagnostic endoscopic imaging support program for causing a computer to function as a three-dimensional image data obtaining section that obtains three-dimensional image data of a subject, a tubular tissue shape data obtaining section that extracts and obtains tubular tissue shape data representing a shape of a tubular tissue in the subject from the three-dimensional image data obtained by the three-dimensional image data obtaining section, an endoscope route data obtaining section that obtains endoscope route data representing a route of an endoscope inserted into the subject, and a matching section that performs matching between the tubular tissue shape data and the endoscope route data.

According to the diagnostic endoscopic imaging support apparatus, method, and program of the present invention, three-dimensional image data of a subject is obtained, then tubular tissue shape data representing a shape of a tubular tissue in the subject are extracted and obtained from the three-dimensional image data, endoscope route data representing a route of an endoscope inserted into the subject are also obtained, and matching between the tubular tissue shape data and the endoscope route data is performed. While in the past, only the tip position of an endoscope was known, this allows also the route the endoscope has passed through the tubular tissue to be identified, and by performing matching between the endoscope route data representing the route and the tubular tissue shape data, influence of deformations in a soft tissue, such as a large intestine and the like, during an operation may be reduced and the position in the three-dimensional image corresponding to the actual tip position of the endoscope may be identified more accurately.

In the diagnostic endoscopic imaging support apparatus of the present invention described above, if a configuration is adopted in which the route of the endoscope in the subject is displayed within a three-dimensional stereoscopic image or a tomographic image of the tubular tissue based on the three-dimensional image data, the endoscope route data, and a result of the matching in the matching section, the tip position of the endoscope may be visually understood more accurately.

Further, if a configuration is adopted in which, when the route of the endoscope in the subject is changed, the matching section obtains a variation in the shape and performs the matching using the variation, the matching may be performed only within the variation range, so that the matching may be speeded up in comparison with the case in which the matching is performed over the entire endoscope route data.

Still further, if a configuration is adopted in which information of distance from the insertion opening of the endoscope to the tip of the endoscope inserted into the subject is obtained and the matching is performed using the information of distance, obviously erroneous matching may be avoided.

Further, if a configuration is adopted in which tip position information of the endoscope in a coordinate of the three-dimensional image data is obtained based on a result of the matching, then virtual endoscopic image data virtually generated on the assumption that imaging is performed at the tip position of the endoscope are obtained based on the tip position information and the three-dimensional image data, and a virtual endoscopic image based on the virtual endoscopic image data and a real endoscopic image actually captured by the endoscope are displayed, a virtual endoscopic image at the position corresponding to the actual tip position of the endoscope may be displayed, so that more accurate navigation may be performed.

BEST MODE FOR CARRYING OUT THE INVENTION

Figure 1:
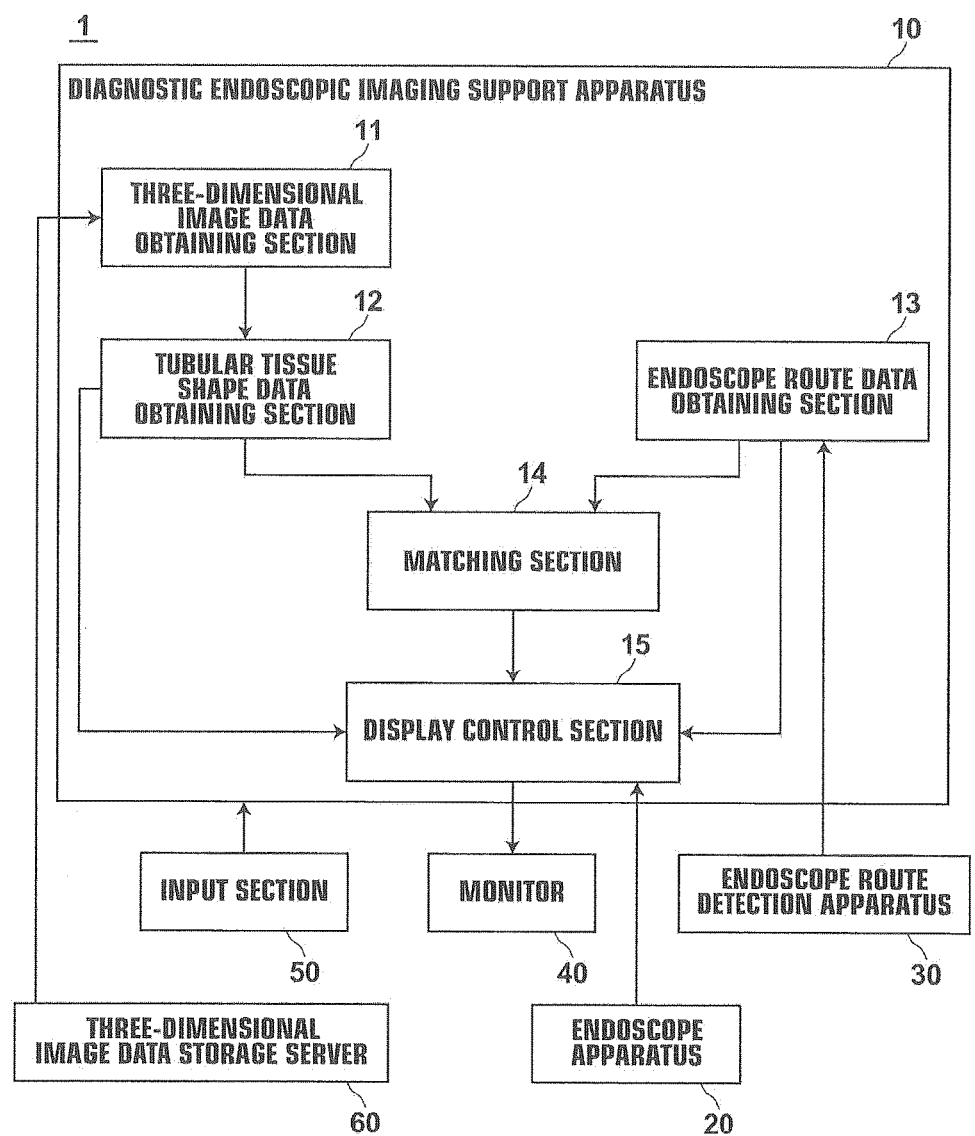
FIG. 1 is a block diagram of a diagnostic endoscopic imaging support system that uses a first embodiment of the present invention, illustrating a schematic configuration thereof.

Hereinafter, a diagnostic endoscopic imaging support system that uses a first embodiment of the diagnostic endoscopic imaging support apparatus, diagnostic endoscopic imaging support program, and diagnostic endoscopic imaging support method will be described in detail with reference to the accompanying drawings. FIG. 1 is a block diagram of the di agnostic endoscopic imaging support system that uses the first embodiment, illustrating a schematic configuration thereof.

As illustrated in FIG. 1, the diagnostic endoscopic imaging support system 1 includes a diagnostic endoscopic imaging support apparatus 10, an endoscope apparatus 20, an endoscope route detection apparatus 30, a monitor 40, an input section 50, and a three-dimensional image data storage server 60.

The diagnostic endoscopic imaging support apparatus 10 is configured by installing a diagnostic endoscopic imaging support program on a computer. The diagnostic endoscopic imaging support apparatus 10 includes a central processing unit (CPU), a semiconductor memory, storage devices, such as a hard disk on which the diagnostic endoscopic imaging support program is installed, a SSD (Solid State Drive), and the like. The hardware described above forms a three-dimensional image data obtaining section 11 (three-dimensional image data obtaining means), a tubular tissue shape data obtaining section 12 (tubular tissue shape data obtaining means), an endoscope route data obtaining section 13 (endoscope route data obtaining means), a matching section 14 (matching means), and a display control section 15 (display control means) shown in FIG. 1. Then, each section described above operates when the diagnostic endoscopic imaging support program installed on the hard disk is executed by the central processing unit.

The three-dimensional image data obtaining section 11 obtains three-dimensional image data of a subject captured in advance such as, before an operation or an examination using the endoscope apparatus 20. The three-dimensional image data may include, for example, volume data reconstructed from slice data outputted from CT equipment, MRI (Magnetic Resonance Imaging) equipment, and the like, or volume data outputted from MS (Multi Slice) CT equipment or cone beam CT equipment. The three-dimensional image data are stored in the three-dimensional image data storage server 60 in advance with identification information of the subject, and the three-dimensional image data obtaining section 11 reads out the three-dimensional image data corresponding to the identification information of a subject inputted at the input section 50 from the three-dimensional image data storage server 60.

The tubular tissue shape data obtaining section 12 receives the three-dimensional image data obtained by the three-dimensional image data obtaining section 11, and extracts and obtains tubular tissue shape data representing a shape of a tubular tissue in the subject from the received three-dimensional image data. The tubular tissue may be, for example, a large intestine, a small intestine, or a bronchus, but not limited to this, and it may be the other tubular tissue. In the present embodiment, it is assumed that large intestine shape data are extracted and obtained.

The large intestine shape data may be specifically extracted in the following manner. First, a plurality of sets of axial image data of cross-sections perpendicular to the body axis is obtained based on the three-dimensional image data. Then, processing for separating outside body area and inside body area with reference to the body surface is performed on each of the axial image data by a known method. For example, binarization processing is performed on the inputted axial image data, then a contour is extracted by contour extraction processing, and the inside the extracted contour is extracted as the body (human body) area. Next, binarization processing by threshold is performed on the axial image data of the body area to extract a large intestine region candidate in each of the axial image data. More specifically, the binarization processing is performed by setting a threshold value (e.g., less than or equal to −600) corresponding to the CT value of the air, because air is included in the tube of large intestine, and the air region in the body in each axial image data is extracted as the large intestine region candidate. Finally, only portions of the extracted large intestine region candidates in the body that can be connected between each of the axial image data are extracted as the large intestine region, whereby the three-dimensional image data of the large intestine region are obtained. The method of obtaining the three-dimensional image of the large intestine region is not limited to that described above and the other known method, such as the region growing method, level set method, and the like, may be used.

Then, the tubular tissue shape data obtaining section 12 obtains tree-structure data of the large intestine as large intestine shape data by thinning the three-dimensional image data of the large intestine region obtained in the manner described above and assuming the center line of the large intestine. Any known method may be used for the thinning processing and, for example, the methods described in M. Yasue et al., "Thinning Algorithms for Three-Dimensional Gray Images and Their Application to Medical Images with Comparative Evaluation of Performance", Journal of IEICE, J79-D-H (10):1664-1674, 1996 and T. Saito et al., "An improvement of Three Dimensional Thinning Method Using a Skeleton Based on the Euclidean Distance Transformation: A Method to Control Spurious Branches" Journal of IEICE, 2001 may be used.

The endoscope route data obtaining section 13 obtains detection information of the endoscope apparatus 20 in the subject detected by the endoscope route detection apparatus 30 and obtains endoscope route data based on the detection information. More specifically, detection information of magnetic markers provided in the endoscope apparatus 20 is obtained in the present embodiment, but the endoscope route data obtaining section 13 obtains line segment structure data obtained by approximating the detection information of the magnetic markers by a spline curve as the endoscope route data, as will be described later in detail.

Since a flexible endoscope apparatus is used as the endoscope apparatus 20 in the present embodiment, the endoscope route data described above may also be endoscope shape data representing a shape of the endoscope apparatus 20. In the case where a so-called capsule endoscope apparatus is used as the endoscope apparatus 20, the data representing the route along which the capsule endoscope apparatus passed through the large intestine are obtained as the endoscope route data described above.

The matching section 14 obtains the large intestine shape data outputted from the tubular tissue shape data obtaining section 12 and the endoscope route data outputted from the endoscope route data obtaining section 13 and performs matching between the obtained large intestine shape data and endoscope route data. The term "matching" as used herein refers to positional alignment processing between a position of a large intestine represented by three-dimensional image data of a large intestine region obtained in advance prior to an operation or an examination and an actual position of the endoscope apparatus 20 in the large intestine inserted into the subject during the operation or examination.

Figure 2:
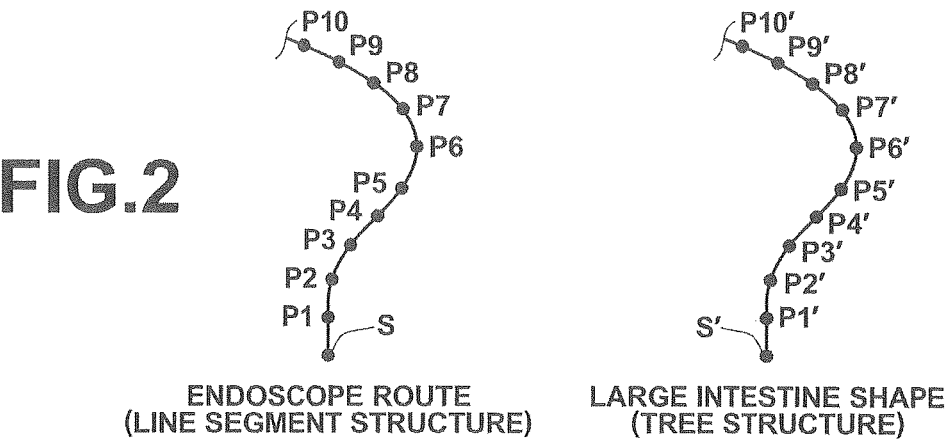
FIG. 2 is a drawing for explaining an example method of matching between large intestine shape data and endoscope route data.

More specifically, as illustrated in FIG. 2, matching candidate points P1, P2, P3, - - - are set on the endoscope route (line segment structure) at a sufficiently fine range interval of 5 mm to 1 cm and matching candidate points P1', P2', P3', - - - are set on the large intestine shape (tree structure) at a similar range interval.

Then, with respect to each matching candidate point on the endoscope route, the curvature is calculated by using coordinate values of several matching candidates before and after the target matching candidate point. That is, for example, the curvature of the matching candidate point P4 on the endoscope route is calculated using the coordinate values of the matching candidate points P1, P2, P3, P4, P6, P7 located before and after the matching candidate P4 and, in this way, the curvature is calculated for each matching candidate point.

Figure 3:
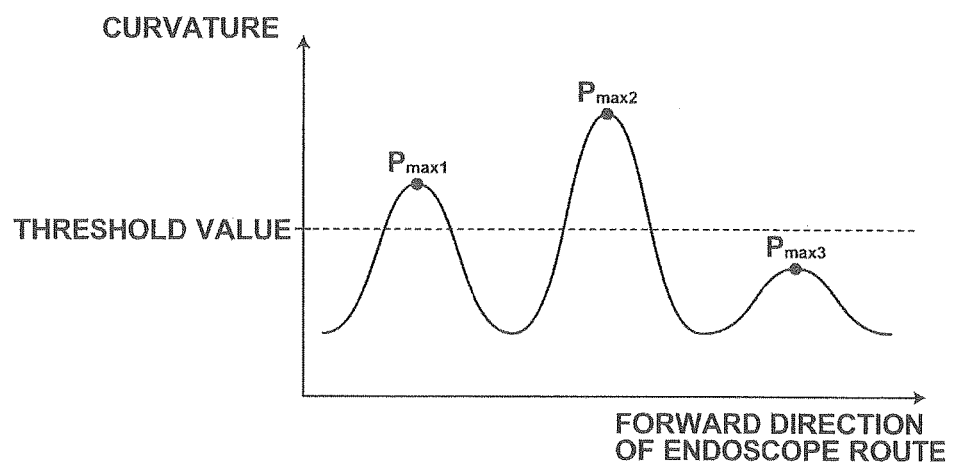
FIG. 3 is a drawing for explaining an example method of matching between large intestine shape data and endoscope route data.

Next, using the curvature of each matching candidate point calculated in the manner described above, local maximum points $P_{max1}$, $P_{max2}$, $P_{max3}$, - - - are calculated, as shown in FIG. 3. Then, among the local maximum points $P_{max1}$, $P_{max2}$, $P_{max3}$, - - -, a maximum point greater than or equal to a preset threshold value is obtained as a target matching point. That is, in the case of FIG. 3, among the local maximum points $P_{max1}$, $P_{max2}$, $P_{max3}$, - - -, only the $P_{max1}$, $P_{max2}$ are obtained as the target matching points.

In the meantime, with respect to each matching candidate point on the large intestine shape, the curvature is calculated in the manner described above, then local maximum points are calculated, and among the local maximum points, a local maximum point greater than or equal to a threshold value is obtained as a target matching point.

Then, matching is performed by correlating the target matching point group on the endoscope route and the target matching point group on the large intestine shape in order from the insertion position S, S' of the endoscope. The local maximum point described above is highly likely a point where the endoscope apparatus 20 or the large intestine is curved, or a point where the other tubular tissue is branched, and such a curved point of the large intestine is a portion that does not practically move in the subject and, therefore, may be used as a characteristic amount of the endoscope apparatus 20 and large intestine shape.

In the aforementioned matching, probable matching may be performed by considering the relationship between the actually inserted length of the endoscope apparatus 20 into the subject and the distance of the endoscope apparatus 20 from the insertion opening in the large intestine shape data, in order to avoid obviously erroneous matching. More specifically, the matching may be performed between target matching points located about 10 cm from the position corresponding to the actually inserted length of the endoscope apparatus 20 in consideration of the extension and shrinkage of the large intestine. The actually inserted length of the endoscope apparatus 20 may be obtained automatically by providing a sensor or the like in the in-body insertion section of the endoscope apparatus 20, or an index such as a scale may be provided on the in-body insertion section and a value read by the user may be inputted using the input section 50.

The matching in the matching section 14 is performed in real time when the route of the in-body insertion section of the endoscope apparatus 20 is changed. More specifically, the matching is performed in real time each time the endoscope route is incremented by a predetermined length.

The matching in the matching section 14 is not necessarily performed in real time between the entire large intestine shape data and endoscope route data, and if the route of the endoscope apparatus 20 in the subject is changed, more specifically, if the endoscope route is incremented, the amount of increment may be obtained and the matching may be performed only within the range of the increment while the matching may not be performed in the other range. For example, if the distance of the endoscope route from the insertion opening is changed from 20 cm to 30 cm, the matching may be performed only for the range from 20 cm to 30 cm of the endoscope route, and for the range from 0 to 20 cm, the previous matching result may be used without newly performing the matching. This may speed up the matching.

The method of matching between the endoscope route data and the large intestine shape data is not limited to that described above, and other known methods may also be used.

The display control section 15 receives the three-dimensional image data of the large intestine region obtained by the tubular tissue shape data obtaining section 12, then performs volume rendering or surface rendering on the three-dimensional image data, and displays the three-dimensional stereoscopic image of the entire large intestine by a voxel model or a surface model on the monitor 40. Further, the display control section 15 receives the endoscope route data obtained by the endoscope route data obtaining section 13 and displays a route (shape) image of the endoscope apparatus 20 in the three-dimensional stereoscopic image of the entire large intestine based on the endoscope route data and a result of the matching in the matching section 14.

More specifically, the display control section 15 transforms the coordinates of the endoscope route data to the coordinates of the three-dimensional stereoscopic image based on the result of the matching in the matching section 14 and displays the route image of the endoscope apparatus 20 on the monitor 40 using the transformed coordinates.

In the present embodiment, the route of the endoscope apparatus 20 is displayed in the three-dimensional stereoscopic image of the entire large intestine, but not limited to this and the route image of the endoscope apparatus 20 may be displayed in a cross-sectional image of the large intestine. As for the cross-sectional image of the large intestine, an image of any cross-section may be used, such as any oblique cross-section, as well as orthogonal cross-sections, including axial cross-section, sagittal cross-section, coronal cross-section, and the like. As for the method of displaying the route (shape) image of the endoscope apparatus 20, the entire route image may be projected onto the cross-section or only a portion of the route image near the cross-section may be projected onto the cross-section to improve viewability.

The display control section 15 also displays a real endoscopic image in the large intestine captured by the endoscope apparatus 20 on the monitor 40.

As for the endoscope apparatus 20, flexible endoscope apparatuses, such as bronchoscope, large intestine endoscope, small intestine endoscope, and the like, and capsule endoscope apparatuses may be used. As for the small intestine endoscope, a double balloon endoscope or a single balloon endoscope may be used. In the present embodiment, the large intestine endoscope apparatus is used as described above.

The endoscope apparatus 20 includes an element corresponding to the element of the endoscope route detection apparatus 30. For example, in the case where the endoscope route detection apparatus 30 detects route information of the endoscope apparatus 20 using a magnetic sensor, magnetic markers are provided at a regular interval on the in-body insertion section of the endoscope apparatus 20. Not limited to the aforementioned example, and the endoscope apparatus 20 may also include the other structures that allow the endoscope route detection apparatus 30 to detect route information of the endoscope apparatus 20.

The endoscope route detection apparatus 30 detects route information of the endoscope apparatus 20. More specifically, the endoscope route detection apparatus 30 includes, for example, a magnetic sensor like that described above and detects route (shape) information of the endoscope apparatus 20 by detecting the magnetic markers provided on the in-body insertion section of the endoscope apparatus 20 by the magnetic sensor set on the body surface of the subject. Note that the endoscope route detection apparatus 30 is not limited to the aforementioned endoscope route detection apparatus that detects the endoscope apparatus 20 by a magnetic sensor, and it may be an endoscope route detection apparatus that detects the endoscope apparatus 20 by an optical sensor. If a capsule endoscope apparatus is used as the endoscope apparatus 20, a configuration may be adopted, for example, in which a detection result of an acceleration sensor provided in the capsule endoscope apparatus is received by wireless communication and route information of the capsule endoscope is detected based on the received result.

The input section 50 receives input of given information of the user and is constituted by a pointing device such as a keyboard or a mouse.

Figure 4:
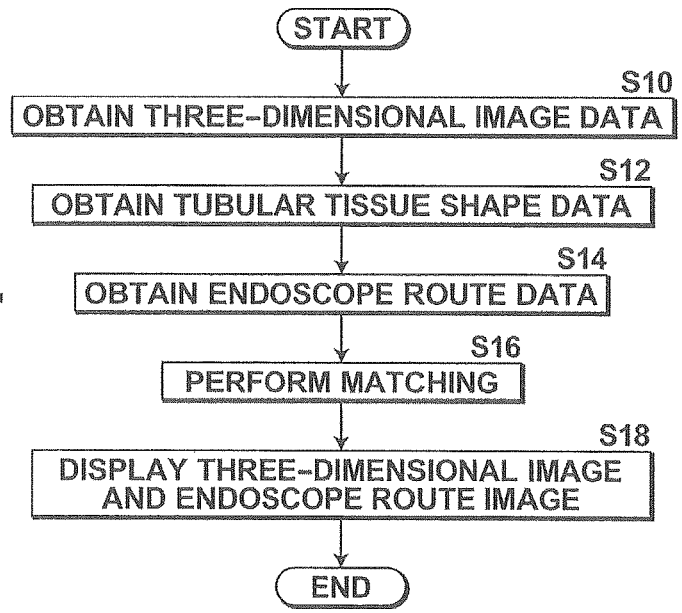
FIG. 4 is a flowchart for explaining an operation of the diagnostic endoscopic imaging support system that uses a first embodiment of the present invention.

An operation of the diagnostic endoscopic imaging support system that uses the first embodiment of the present invention will now be described with reference to the flowchart shown in FIG. 4.

First, subject identification information is inputted at the input section 50, and the three-dimensional image data obtaining section 11 of the diagnostic endoscopic imaging support system 10 reads out and obtains three-dimensional image data corresponding to the inputted subject identification information from the three-dimensional image data storage server 60 (S10).

The three-dimensional image data obtained by the three-dimensional image data obtaining section 11 is inputted to the tubular tissue shape data obtaining section 12 and the tubular tissue shape data obtaining section 12 extracts and obtains large intestine shape data based on the inputted three-dimensional image data (S12).

In the meantime, the in-body insertion section of the endoscope apparatus 20 is inserted into the large intestine of the subject and imaging of the inside of the large intestine is started. At this time, route (shape) information of the endoscope apparatus 20 is detected by the endoscope route detection apparatus 30 and the detection information is obtained by the endoscope route data obtaining section 13. More specifically, for example, magnetic markers provided on the endoscope apparatus 20 are detected by a magnetic sensor of the endoscope route detection apparatus 30 and the detection information is obtained by the endoscope route data obtaining section 13 and the endoscope route data obtaining section 13 generates and obtains endoscope route data based on the detection information (S14).

Then, the large intestine shape data obtained by the tubular tissue shape data obtaining section 12 and the endoscope route data obtained by the endoscope route data obtaining section 13 are inputted to the matching section 14 and the matching section 14 performs matching using the inputted data (S16). The method of the matching in the matching section 14 is as described above.

Figure 5:
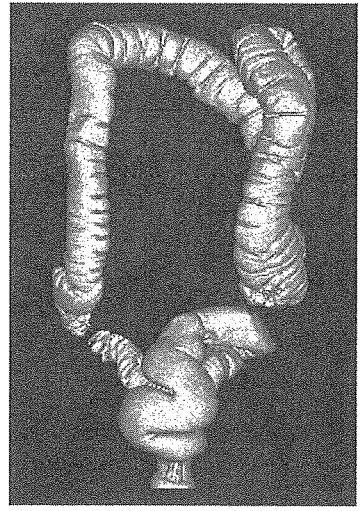
FIG. 5 illustrates an example front view of a three-dimensional stereoscopic image of the entire large intestine.
Figure 6:
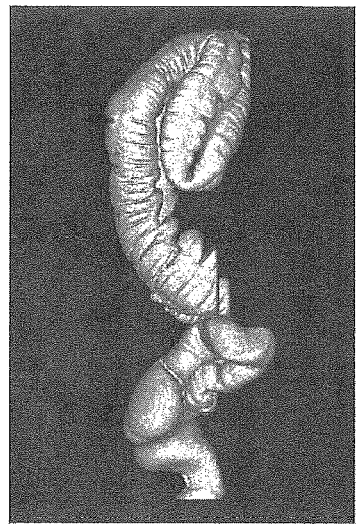
FIG. 6 illustrates an example side view of a three-dimensional stereoscopic image of the entire large intestine.
Figure 7:
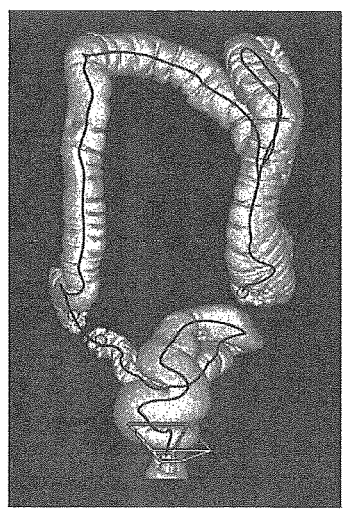
FIG. 7 illustrates an image in which a tree structure image is superimposed on a front view of a three-dimensional stereoscopic image of the entire large intestine.
Figure 8:
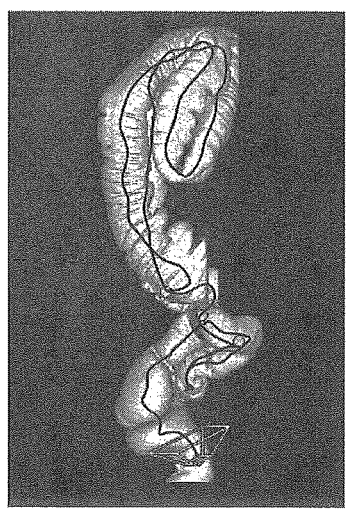
FIG. 8 illustrates an image in which a tree structure image is superimposed on a side view of a three-dimensional stereoscopic image of the entire large intestine.

Next, the three-dimensional image data of the large intestine region obtained by the tubular tissue shape data obtaining section 12 are inputted to the display control section 15 and the display control section 15 performs volume rendering or surface rendering on the three-dimensional image data of the large intestine region and displays a three-dimensional stereoscopic image of the entire large intestine on the monitor 40. FIG. 5 illustrates an example front view of a three-dimensional stereoscopic image of the entire large intestine and FIG. 6 illustrates an example side view of a three-dimensional stereoscopic image of the entire large intestine. The front view shown in FIG. 5 and the side view shown in FIG. 6 may be displayed side-by-side or in a switching manner by receiving a display switching instruction from the user at the input section 50. Further, a tree structure image represented by the aforementioned tree structure data may be displayed superimposed on the three-dimensional stereoscopic image of the entire large intestine, as shown in FIGS. 7 and 8.

Figure 9:
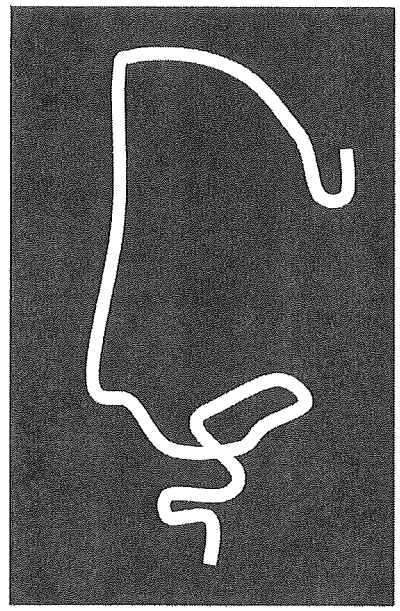
FIG. 9 illustrates an example front view of an endoscope route image represented by endoscope route image data.
Figure 10:
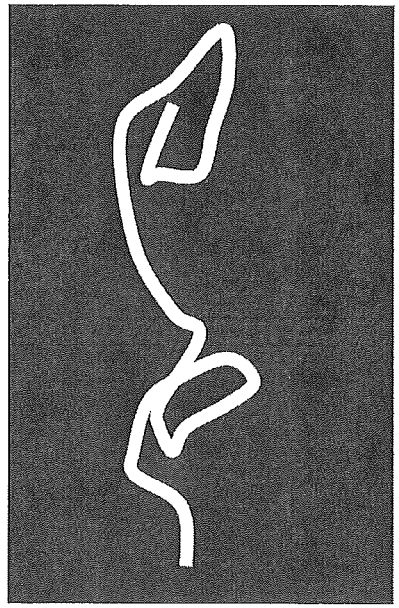
FIG. 10 illustrates an example side view of an endoscope route image represented by endoscope route image data.

Further, the endoscope route data obtained in the matching section 14 is inputted to the display control section 15 and the display control section 15 generates endoscope route image data based on the inputted endoscope route data FIG. 9 illustrates an example front view of an endoscope route image represented by the endoscope route image data and FIG. 10 illustrates an example side view of the endoscope route image represented by the endoscope route image data.

Figure 11:
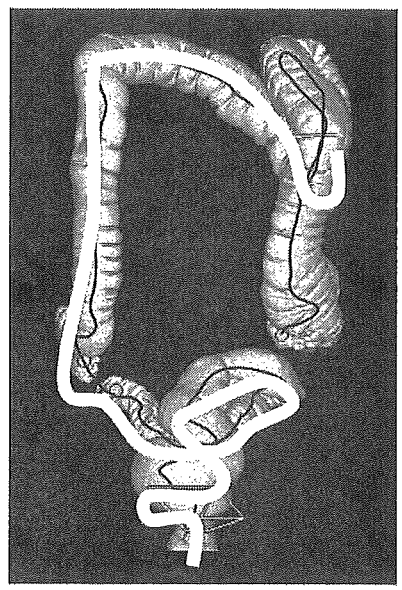
FIG. 11 illustrates an example front view in which an endoscope route image is superimposed on a three-dimensional stereoscopic image of the entire large intestine.
Figure 12:
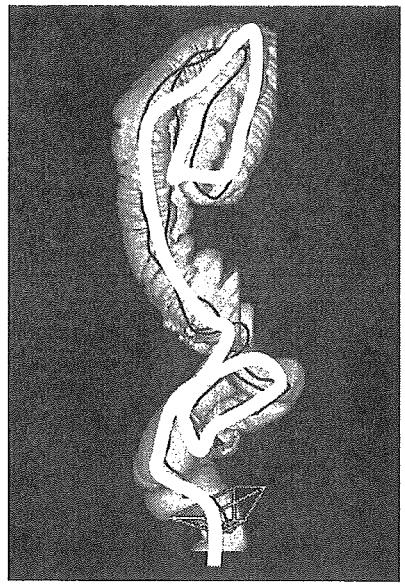
FIG. 12 illustrates an example side view in which an endoscope route image is superimposed on a three-dimensional stereoscopic image of the entire large intestine.

Then, the display control section 15 displays the endoscope route image superimposed within the three-dimensional stereoscopic image of the entire large intestine based on the endoscope route image data and the matching result in the matching section 14 (S18) FIG. 11 illustrates an example front view in which the endoscope route image is superimposed within the three-dimensional stereoscopic image of the entire large intestine, and FIG. 12 illustrates an example side view in which the endoscope route image is superimposed within the three-dimensional stereoscopic image of the entire large intestine. The front view shown in FIG. 11 and the side view shown in FIG. 12 may also be displayed side-by-side or in a switching manner by receiving a display switching instruction from the user at the input section 50.

Further, the display control section 15 displays an endoscopic image of the large intestine captured by the endoscope apparatus 20 together with the three-dimensional stereoscopic image and the endoscope route image. The three-dimensional stereoscopic image with the endoscope route image and the endoscopic image of the large intestine may also be displayed side-by-side or in a switching manner by receiving a display switching instruction from the user at the input section 50.

According to the diagnostic endoscopic imaging support system that uses the first embodiment of the present invention described above, matching is performed between the endoscope route data and the tubular tissue shape data, so that influence of deformations in a soft tissue, such as a large intestine and the like, during an operation may be reduced and the position in the three-dimensional image corresponding to the actual tip position of the endoscope may be identified more accurately. Then, by displaying images like those shown in FIGS. 11 and 12, the position in the three-dimensional image corresponding to the actual tip position of the endoscope may be visually understood more accurately. In the case where the large intestine is three-folded in a front-back direction, as shown in FIGS. 11 and 12, in particular, it is difficult to understand in which section of the three-folded portion the tip of the endoscope 20 is actually located only by the endoscope tip position coordinates. But, as described above, by performing matching between the endoscope route data and the tubular tissue shape data, it is easily understood that the tip of the endoscope apparatus 20 is located in the middle section of the three-folded portion, as shown in FIG. 12.

The endoscope route image displayed within the three-dimensional stereoscopic image may be displayed or hidden by receiving a display switching instruction from the user at the input section 50 and switching according to the instruction.

Figure 13:
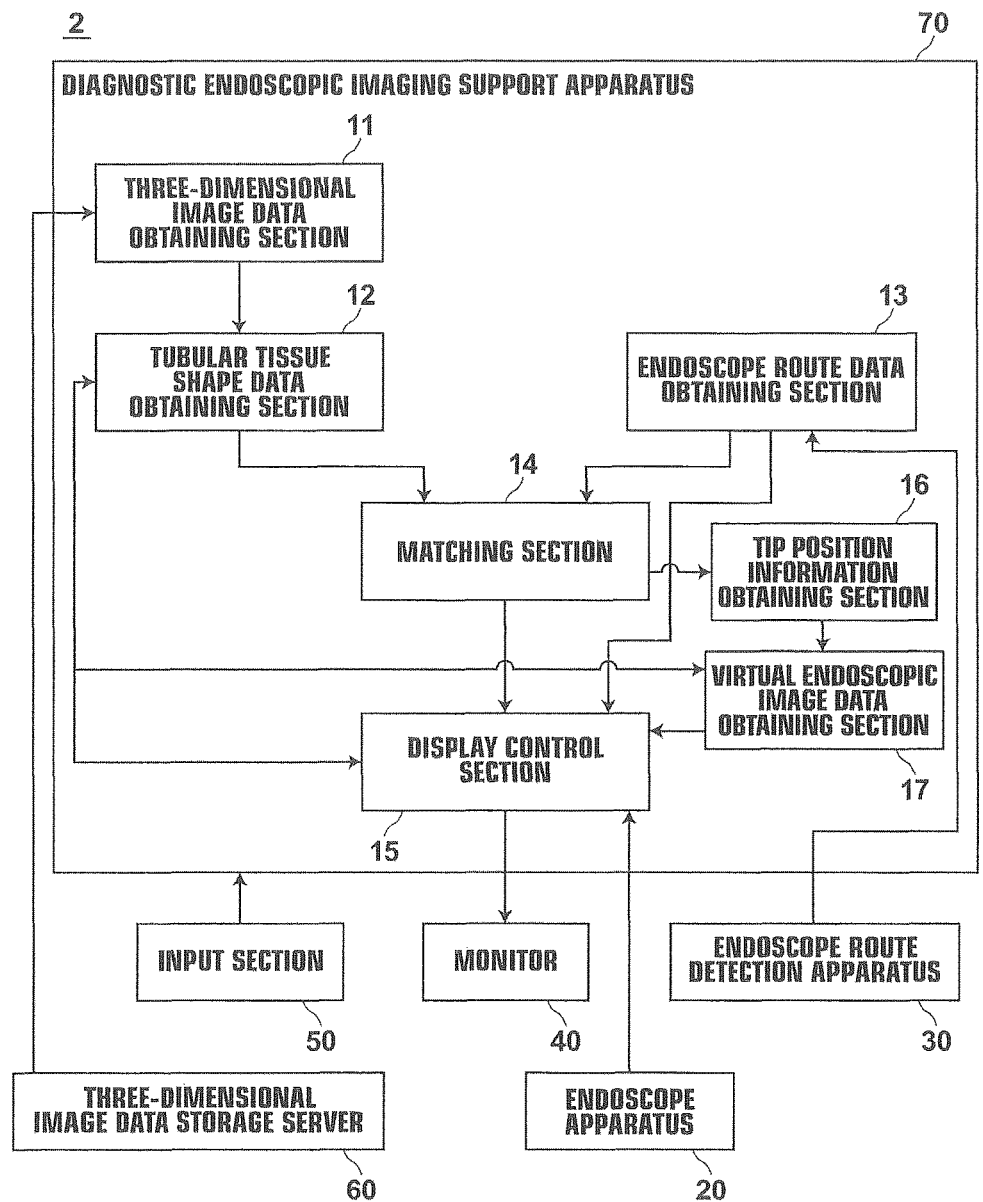
FIG. 13 is a block diagram of a diagnostic endoscopic imaging support system that uses a second embodiment of the present invention, illustrating a schematic configuration thereof.

Next, a diagnostic endoscopic imaging support system that uses a second embodiment of the present invention will be described. FIG. 13 is a block diagram of a diagnostic endoscopic imaging support system that uses a second embodiment of the present invention, illustrating a schematic configuration thereof.

The second diagnostic endoscopic imaging support system 2 differs from the first diagnostic endoscopic imaging support system in that it displays a virtual endoscopic image. The other structures are identical to the first diagnostic endoscopic imaging support system 1 and the following description will focus on the difference.

A diagnostic endoscopic imaging support apparatus 70 of the second diagnostic endoscopic imaging support system 2 further includes a tip position information obtaining section 16 (tip position information obtaining means) and a virtual endoscopic image data obtaining section 17 (virtual endoscopic image data obtaining means) with respect to the diagnostic endoscopic imaging support apparatus 10 of the first embodiment.

The tip position information obtaining section 16 obtains a tip position coordinate of the in-body insertion section of the endoscope apparatus 20 in the coordinate of the three-dimensional stereoscopic image of the large intestine based on the matching result in the matching section 14 as tip position information.

The virtual endoscopic image data obtaining section 17 receives the three-dimensional image data of the large intestine region obtained in the tubular tissue shaped data obtaining section 12 and the tip position information obtained in the tip position information obtaining section 16. Then, virtual endoscopic image data obtaining section 17 obtains projection image data by central projection, which are image data generated by projecting, with the tip position information obtained by the tip position information obtaining section 16 as the viewpoint, three-dimensional image data on a plurality of visual lines extended radially from the viewpoint onto a predetermined projection plane. The projection image data are virtual endoscopic image data virtually generated on the assumption that imaging is performed at the tip position of the endoscope obtained by the tip position information obtaining section 16. As for the specific method of the central projection, for example, the known volume rendering and the like may be used. It is assumed here that the angle of view (visual line range) and the center of the field of view (center in the projection direction) of the virtual endoscopic image data are preset by a user input or the like.

Then, the virtual endoscopic image data obtained in the manner described above are inputted to the display control section 15 and the display control section 15 displays a virtual endoscopic image on the monitor 40 based on the inputted virtual endoscopic image data.

Figure 14:
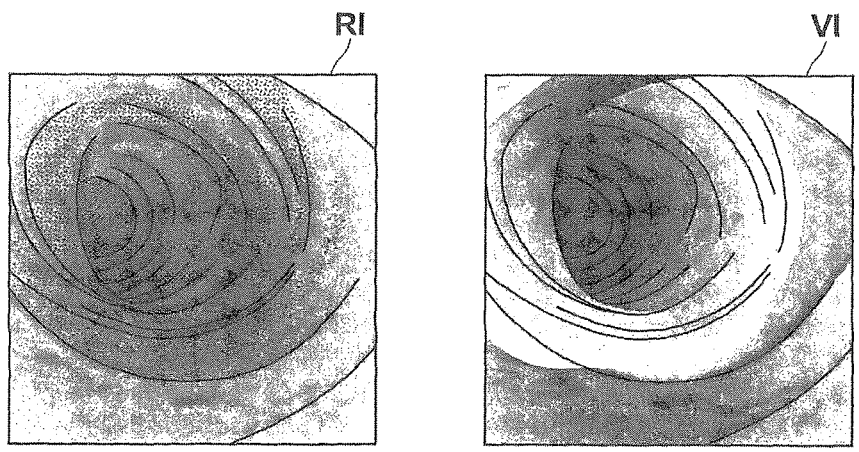
FIG. 14 illustrates an example display form in which a real endoscopic image RI actually captured and a virtual endoscopic image VI are displayed side-by-side.
Figure 15:
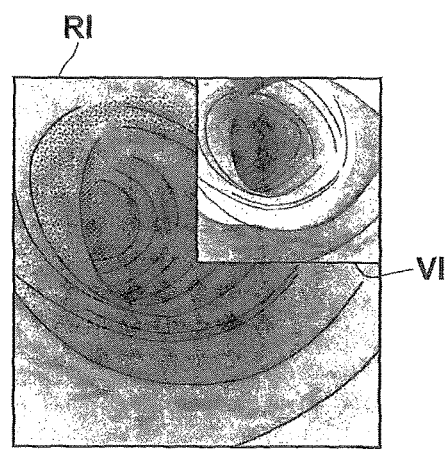
FIG. 15 illustrates an example display form in which a virtual endoscopic image VI is displayed on the display screen of a real endoscopic image RI actually captured.

Note that, at this time, the real endoscopic image RI actually captured by the endoscope apparatus 20 and the virtual endoscopic image VI may be displayed side-by-side, as shown in FIG. 14, or the virtual endoscopic image VI may be displayed in the display screen of the real endoscopic image RI actually captured, as shown in FIG. 15. Otherwise, blending display may be performed in which a virtual endoscopic image subjected to semi-transparent processing is superimposed on the real endoscopic image RI.

In the virtual endoscopic image VI, for example, a lesion area of the large intestine is highlighted or a guide display is provided for guiding which direction the in-body insertion section of the endoscope apparatus 20 should proceed.

In the diagnostic endoscopic imaging support system of the second embodiment, the three-dimensional stereoscopic image of the large intestine with the endoscope route image, the real endoscopic image RI of the large intestine, and the virtual endoscopic image VI may be displayed side-by-side or each of the four images may be displayed or hidden by receiving a display switching instruction from the user at the input section 50 and switching according to the instruction.

According to the diagnostic endoscopic imaging support system of the second embodiment of the present invention, tip position information of the endoscope is obtained in the coordinate of the three-dimensional image data based on a result of the matching, then virtual endoscopic image data are obtained based on the tip position information and the three-dimensional image data, and a virtual endoscopic image based on the virtual endoscopic image data and a real endoscopic image actually captured by the endoscope are displayed. This allows a virtual endoscopic image at the position corresponding to the actual tip position of the endoscope to be displayed, thereby allowing more accurate navigation.

What is claimed is:

1. A diagnostic endoscopic imaging support apparatus, comprising:
    a processor configured to execute a process, the process comprising:
        obtaining three-dimensional image data of a subject;
        extracting and obtaining tubular tissue shape data representing a shape of a tubular tissue in the subject from the three-dimensional image data;
        obtaining endoscope route data representing a set of positions along a route of an endoscope inserted into the subject and including a position of a tip of the endoscope,
            wherein the position of the tip the endoscope corresponds to a front-most position along said series of positions;
        extracting, from the tubular tissue shape data and the endoscope route data, target points at which curvature of the shape of the tubular tissue indicated by the tubular tissue shape data and curvature of the route of the endoscope indicated by the endoscope route data commonly exceed a predetermined threshold;
        using the extracted target points, performing matching between the shape of the tubular tissue represented by the tubular tissue shape data and the series of positions along the route of the endoscope including the position of the tip of the endoscope represented by the endoscope route data,
            wherein, when the route of the endoscope in the subject is changed, a detection of a variation in the route of the endoscope is made and the matching is performed in real-time for the part of the route of the endoscope for which the variation has been detected, and reuses the result of previous matching for the remaining part of the route without performing the matching anew; and
        transforming the series of positions along the route of the endoscope based on a result of the matching; and
    a display configured to display the transformed series of positions along the route of the endoscope in the subject in an image obtained from the three-dimensional image data.

2. The diagnostic endoscopic imaging support apparatus as claimed in claim 1, wherein the image is a three-dimensional stereoscopic image.

3. The diagnostic endoscopic imaging support apparatus as claimed in claim 1, wherein the image is a cross-sectional image.

4. The diagnostic endoscopic imaging support apparatus as claimed in claim 1, wherein the process further comprises: obtaining tree structure data as the tubular tissue shape data; and performing matching using the tree structure data.

5. The diagnostic endoscopic imaging support apparatus as claimed in claim 4, wherein the process further comprises: obtaining line segment structure data as the endoscope route data; and performing matching of local maximum points of curvature between the line segment structure data and the tree structure data.

6. The diagnostic endoscopic imaging support apparatus as claimed in claim 1, wherein the process further comprises obtaining information of distance from the insertion opening of the endoscope to the tip of the endoscope inserted into the subject and performing the matching using the information of distance.

7. The diagnostic endoscopic imaging support apparatus as claimed in claim 2, wherein the display control section displays the tubular tissue as a surface model.

8. The diagnostic endoscopic imaging support apparatus as claimed in claim 2, wherein the display control section displays the tubular tissue as a voxel model.

9. The diagnostic endoscopic imaging support apparatus as claimed in claim 1, wherein the process further comprises: obtaining tip position information of the endoscope in a coordinate of the three-dimensional image data based on a result of the matching; obtaining virtual endoscopic image data virtually generated on the assumption that imaging is performed at the tip position of the endoscope based on the tip position information and the three-dimensional image data; and displaying, on the display, a virtual endoscopic image based on the virtual endoscopic image data and a real endoscopic image actually captured by the endoscope.

10. The diagnostic endoscopic imaging support apparatus as claimed in claim 2, wherein the process further comprises: obtaining tip position information of the endoscope in a coordinate of the three-dimensional image data based on a result of the matching; obtaining virtual endoscopic image data virtually generated on the assumption that imaging is performed at the tip position of the endoscope based on the tip position information and the three-dimensional image data; and displaying, on the display, a virtual endoscopic image based on the virtual endoscopic image data and a real endoscopic image actually captured by the endoscope.

11. The diagnostic endoscopic imaging support apparatus as claimed in claim 9, wherein the process further comprises displaying, on the display, the virtual endoscopic image and the real endoscopic image side-by-side.

12. The diagnostic endoscopic imaging support apparatus as claimed in claim 9, wherein the process further comprises displaying, on the display, the virtual endoscopic image within the display screen of the real endoscopic image.

13. The diagnostic endoscopic imaging support apparatus as claimed in claim 9, wherein the process further comprises performing, on the display, a blending display of the real endoscopic image and the virtual endoscopic image.

14. The diagnostic endoscopic imaging support apparatus as claimed in claim 1, wherein the endoscope comprises a bronchoscope, a large intestine endoscope, a small intestine endoscope, or a capsule endoscope.

15. The diagnostic endoscopic imaging support apparatus as claimed in claim 1, wherein the tubular tissue comprises a bronchus, a large intestine, or a small intestine.

16. The diagnostic endoscopic imaging support apparatus as claimed in claim 1, wherein the three-dimensional image data comprise Computed Tomography (CT) image data.

17. The diagnostic endoscopic imaging support apparatus as claimed in claim 1, wherein the three-dimensional image data comprise Magnetic Resonance (MR) image data.

18. A diagnostic endoscopic imaging support method, comprising:
by a processor,
obtaining three-dimensional image data of a subject;
extracting and obtaining tubular tissue shape data representing a shape of a tubular tissue in the subject from the three-dimensional image data;
obtaining endoscope route data representing a series of positions along a route of an endoscope inserted into the subject and including a position of a tip of the endoscope,
wherein the position of the tip of the endoscope corresponds to a front-most position along said series of positions;
extracting, from the tubular tissue shape data and the endoscope route data, target points at which curvature of the shape of the tubular tissue indicated by the tubular tissue shape data and curvature of the route of the endoscope indicated by the endoscope route data commonly exceed a predetermined threshold;
using the extracted target points, performing matching between the shape of the tubular tissue represented by the tubular tissue shape data and the series of positions along the route of the endoscope including the position of the tip of the endoscope represented by the endoscope route data,
wherein, when the route of the endoscope in the subject is changed, a detection of a variation in the route of the endoscope is made and the matching is performed in real-time for the part of the route of the endoscope for which the variation has been detected, and reuses the result of previous matching for the remaining part of the route without performing the matching anew; and
transforming the series of positions along the route of the endoscopic based on a result of the matching; and displaying the transformed series of positions along the route of the endoscope in the subject in an image obtained from the three-dimensional image data.

19. A non-transitory computer readable medium on which is recorded a diagnostic endoscopic imaging support program for causing a computer to execute a process, the process comprising:
obtaining three-dimensional image data of a subject;
extracting and obtaining tubular tissue shape data representing a shape of a tubular tissue in the subject from the three-dimensional image data;
obtaining endoscope route data representing a set of positions alone a route of an endoscope inserted into the subject and including a position of a tip of the endoscope,
wherein the position of the tip of the endoscope corresponds to a front-most position along said series of positions;
extracting, from the tubular tissue shape data and the endoscope route data, target points at which curvature of the shape of the tubular tissue indicated by the tubular tissue shape data and curvature of the route of the endoscope indicated by the endoscope route data commonly exceed a predetermined threshold;
using the extracted target points, performing matching between the shape of the tubular tissue represented by the tubular tissue shape data and the series of positions along the route of the endoscope including the position of the tip of the endoscope represented by the endoscope route data,
wherein, when the route of the endoscope in the subject is changed, a detection of a variation in the route of the endoscope is made and the matching is performed in real-time for the part of the route of the endoscope for which the variation has been detected, and reuses the result of previous matching for the remaining part of the route without performing the matching anew; and
transforming the series of positions along the route of the endoscope based on a result of the matching; and
controlling a display to display the transformed series of positions along the route of the endoscope in the subject in an image obtained from the three-dimensional image data.

* * * * *